(12) United States Patent
Yoo

(10) Patent No.: US 10,143,296 B2
(45) Date of Patent: Dec. 4, 2018

(54) MOUTHPIECE TYPE OF ELECTRIC TOOTHBRUSH

(71) Applicant: Hee Jang Yoo, Incheon (KR)

(72) Inventor: Hee Jang Yoo, Incheon (KR)

(*) Notice: Subject to any disclaimer, the term of this patent is extended or adjusted under 35 U.S.C. 154(b) by 164 days.

(21) Appl. No.: 15/033,606

(22) PCT Filed: Oct. 28, 2014

(86) PCT No.: PCT/KR2014/010150
§ 371 (c)(1),
(2) Date: Apr. 29, 2016

(87) PCT Pub. No.: WO2015/072676
PCT Pub. Date: May 21, 2015

(65) Prior Publication Data
US 2016/0270892 A1    Sep. 22, 2016

(30) Foreign Application Priority Data

Nov. 18, 2013  (KR) .................. 10-2013-0139944
Nov. 18, 2013  (KR) .................. 10-2013-0139945

(51) Int. Cl.
*A46B 9/04*    (2006.01)
*A61C 17/22*   (2006.01)
(Continued)

(52) U.S. Cl.
CPC .............. *A46B 9/045* (2013.01); *A61C 17/22* (2013.01); *A61C 17/222* (2013.01);
(Continued)

(58) Field of Classification Search
CPC ....... A46B 9/045; A61C 17/22; A61C 17/222; A61C 17/228; A61C 17/3481
(Continued)

(56) References Cited

U.S. PATENT DOCUMENTS 4,585,416 A * 4/1986 DeNiro ............... A46B 1/00
                                                       15/104.93
6,311,358 B1 * 11/2001 Soetewey ........... A46B 9/06
                                                       15/110

(Continued)

FOREIGN PATENT DOCUMENTS

JP  2004-057315 A   2/2004
JP  2012-187377 A  10/2012
(Continued)

*Primary Examiner* — Laura C Guidotti
(74) *Attorney, Agent, or Firm* — Morgan, Lewis & Bockius, LLP

(57) ABSTRACT

A mouthpiece type of electric toothbrush is disclosed. The mouthpiece type of electric toothbrush includes: a toothbrush head that includes a mouthpiece-shaped housing which is provided with upper and lower openings and a blocked intermediate portion, wherein a plurality of first silicone protrusions may be arranged to be spaced apart from each other by a predetermined interval along an inner wall surface of the housing in the upper and lower openings; and a main body that is detachable from the toothbrush head and transmits a vibration to the toothbrush head. The toothbrush head may further include a water-containing pad and an air layer provided at a lower portion of a silicone layer thereof, thus it is possible to easily spread toothpaste through the water-containing pad and to correspond to a size of a user's mouth or oral cavity by adjusting an air amount of the air layer.

7 Claims, 7 Drawing Sheets

(51) Int. Cl.
*A61C 17/34* (2006.01)
*A61C 17/32* (2006.01)

(52) U.S. Cl.
CPC ........ *A61C 17/3481* (2013.01); *A61C 17/228* (2013.01); *A61C 17/32* (2013.01)

(58) Field of Classification Search
USPC .......................... 15/104.93–104.94, 186–188
See application file for complete search history.

(56) References Cited

U.S. PATENT DOCUMENTS

| | | | | |
|---|---|---|---|---|
| 8,234,741 B2 * | 8/2012 | Boyd | ............... | A46B 9/005 |
| | | | | 15/106 |
| 8,359,692 B2 * | 1/2013 | Brewer | ............... | A46B 9/045 |
| | | | | 15/167.2 |
| 2013/0067665 A1 * | 3/2013 | Sowinski | ............... | A46B 9/045 |
| | | | | 15/4 |

FOREIGN PATENT DOCUMENTS

| | | |
|---|---|---|
| KR | 2001-0002595 A | 1/2001 |
| KR | 2002-0071834 A | 9/2002 |
| KR | 2011-0111434 A | 10/2011 |

* cited by examiner

MOUTHPIECE TYPE OF ELECTRIC TOOTHBRUSH

TECHNICAL FIELD

The present invention relates to an electric toothbrush. More particularly, the present invention relates to a mouthpiece type of electric toothbrush to which a toothbrush head of a silicone material is applied.

BACKGROUND ART

Generally, a toothbrush is used for brushing teeth, and the toothbrush is mainly classified into a manual toothbrush and an electric toothbrush.

The manual toothbrush is one in which a user directly moves the toothbrush to brush teeth.

The electric toothbrush is configured so that a circular head rotated by an electric motor installed therein vibrates or rotates to brush teeth.

Recently, the electric toothbrush has been widely popularized, and particularly, the electric toothbrush is very helpful for children and the disabled when they brush their teeth.

However, in case of the conventional electric toothbrush, since a user holds its handle to move it little by little, there is inconvenience when the child or the disabled uses it.

In order to overcome such a drawback, an automatic cleaning apparatus for teeth is disclosed in Korean Patent Laid-Open Publication No. 2002-0071834.

However, the automatic cleaning apparatus for the teeth requires the supply of liquid toothpaste and water, thus its structure is complicated and the manufacturing cost increases.

DISCLOSURE

Technical Problem

The present invention has been made in an effort to provide a mouthpiece type of electric toothbrush that has a simple structure and may be manufactured at a low cost.

In addition, the present invention has been made in an effort to provide a mouthpiece type of electric toothbrush that may prevent growth of bacteria and of which sterilization and disinfection are easily performed by forming a toothbrush head with a silicone material.

The present invention has been made in an effort to provide a mouthpiece type of electric toothbrush that may make gums healthy by massaging the gums while brushing teeth.

The present invention has been made in an effort to provide a mouthpiece type of electric toothbrush that may easily brush the tongue and the palate.

The present invention has been made in an effort to provide a mouthpiece type of electric toothbrush that may be conveniently used by increasing intensity of vibration through a crankshaft even though a size of the housing is small.

The present invention has been made in an effort to provide a mouthpiece type of electric toothbrush that may easily spread toothpaste through a water-containing pad that is further provided and that is adjustable to correspond to a size of a user's mouth or oral cavity by adjusting an air amount of an air layer provided at a lower portion of a silicone layer thereof.

Technical Solution

An exemplary embodiment of the present invention provides a mouthpiece type of electric toothbrush, including: a toothbrush head that includes an mouthpiece-shaped housing which is provided with upper and lower openings and a blocked intermediate portion, wherein a plurality of first silicone protrusions may be arranged to be spaced apart from each other by a predetermined interval along an inner wall surface of the housing in the upper and lower openings; and a main body that is detachable from the toothbrush head and transmits a vibration to the toothbrush head.

The toothbrush head may include a tongue-cleaning portion for cleaning an upper surface of a tongue and a palate, wherein the tongue-cleaning portion may be provided in an inner concave portion of the housing.

A plurality of second silicone protrusions may be respectively formed on upper and lower portions of the tongue-cleaning portion by a predetermined internal.

A plurality of protrusions may be formed on opposite surfaces of an inner intermediate wall of the housing as portions of the housing which molars contact, and a plurality of protrusions may be formed on lateral surfaces of an inner wall of the housing as portions of the housing which incisors contact.

A framework of the housing may be formed of a plastic material, and an outer skin thereof may be formed of a silicone material.

The first and second silicone protrusions may be disposed to have a predetermined interval for foreign matter to pass therethrough, and to have a bumpy surface so as to be easily cleaned.

A groove for detachable coupling with the main body may be formed in the housing.

Another embodiment of the present invention provides a mouthpiece type of electric toothbrush, including: a toothbrush head that includes a mouthpiece-shaped housing which is provided with upper and lower openings and a blocked intermediate portion, wherein a plurality of first silicone protrusions may be arranged to be spaced apart from each other by a predetermined interval along an inner wall surface of the housing in the upper and lower openings, and a plurality of water-containing pads for absorbing water may be provided between the plurality of first silicone protrusions; and a main body that is detachable from the toothbrush head and transmits a vibration to the toothbrush head.

The toothbrush head may include a silicone layer on which the first silicone protrusions are formed in the mouthpiece-shaped housing, and an air layer into which air is injected and which is disposed between the housing and the silicone layer.

The main body may include a motor that vibrates when electric power is applied thereto, and a crankshaft that allows vibration of the motor to be moved up or down.

The toothbrush head may include a tongue-cleaning portion that is configured to clean an upper surface of the tongue and the palate and that is provided in an inner concave portion of the housing.

A plurality of second silicone protrusions may be respectively formed on upper and lower portions of the tongue-cleaning portion by a predetermined internal.

A plurality of protrusions may be formed on opposite surfaces of an inner intermediate wall of the housing as portions of the housing which molars contact, and a plurality of protrusions may be formed on lateral surfaces of an inner wall of the housing as portions of the housing which incisors contact.

The first and second silicone protrusions may be disposed to have a predetermined interval for foreign matter to pass therethrough, and to have a bumpy surface so as to be easily cleaned.

Advantageous Effects

According to an embodiment of the present invention, it is possible to provide a mouthpiece type of electric toothbrush that has a simple structure and may be manufactured at a low cost.

In addition, it is possible to provide a mouthpiece type of electric toothbrush that may be conveniently used by increasing intensity of vibration through a crankshaft even though a size of the housing is small.

Further, it is possible to provide a mouthpiece type of electric toothbrush that may easily spread toothpaste through a water-containing pad and that is adjustable to correspond to a size of a user's mouth or oral cavity by adjusting an air amount of an air layer provided at an lower portion of a silicone layer thereof.

It is also possible to provide a mouthpiece type of electric toothbrush that may prevent growth of bacteria, and of which sterilization and disinfection are easily performed, by forming a toothbrush head with a silicone material.

It is further possible to provide a mouthpiece type of electric toothbrush that may make gums healthy by massaging the gums while brushing teeth.

In addition, it is possible to provide a mouthpiece type of electric toothbrush that may easily brush the tongue and the palate.

MODE FOR INVENTION

Figure 1:
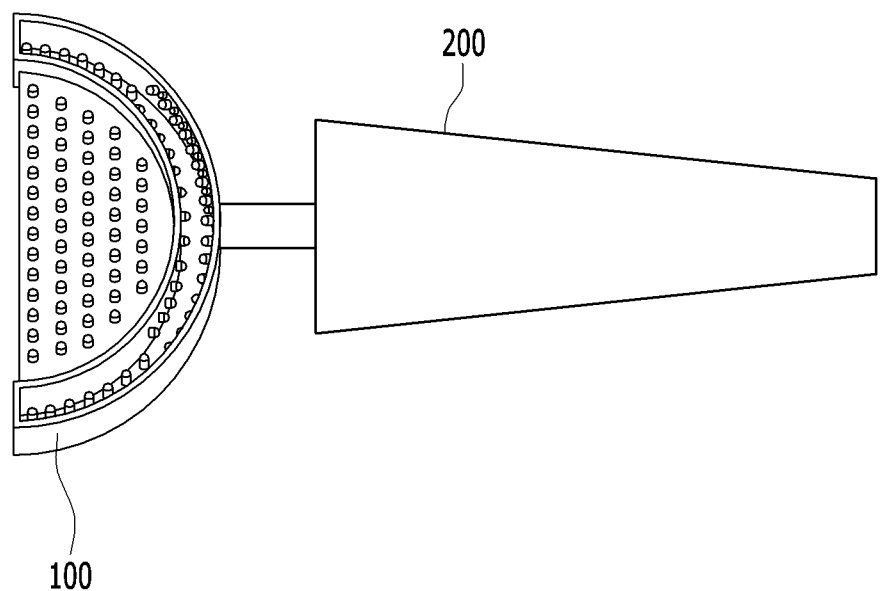
FIG. 1 illustrates a schematic diagram of a mouthpiece type of electric toothbrush according to an exemplary embodiment of the present invention.

In the following detailed description, only certain exemplary embodiments of the present invention have been shown and described, simply by way of illustration. As those skilled in the art would realize, the described embodiments may be modified in various different ways, all without departing from the spirit or scope of the present invention. Accordingly, the drawings and description are to be regarded as illustrative in nature and not restrictive. Like reference numerals designate like elements throughout the specification.

Throughout the specification, unless explicitly described to the contrary, the word "comprise" and variations such as "comprises" or "comprising" will be understood to imply the inclusion of stated elements but not the exclusion of any other elements. In addition, the terms "-er", "-or", and "module" described in the specification mean units for processing at least one function and operation, and can be implemented by hardware components or software components and combinations thereof.

Figure 2:
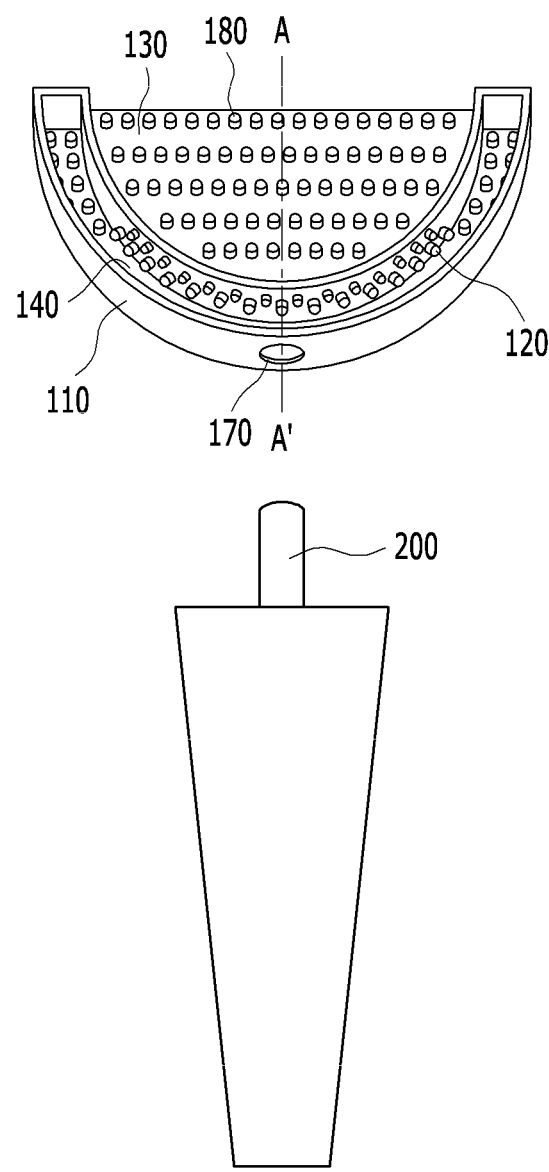
FIG. 2 illustrates a schematic diagram of a toothbrush part of a mouthpiece type of electric toothbrush according to an exemplary embodiment of the present invention.
Figure 3:
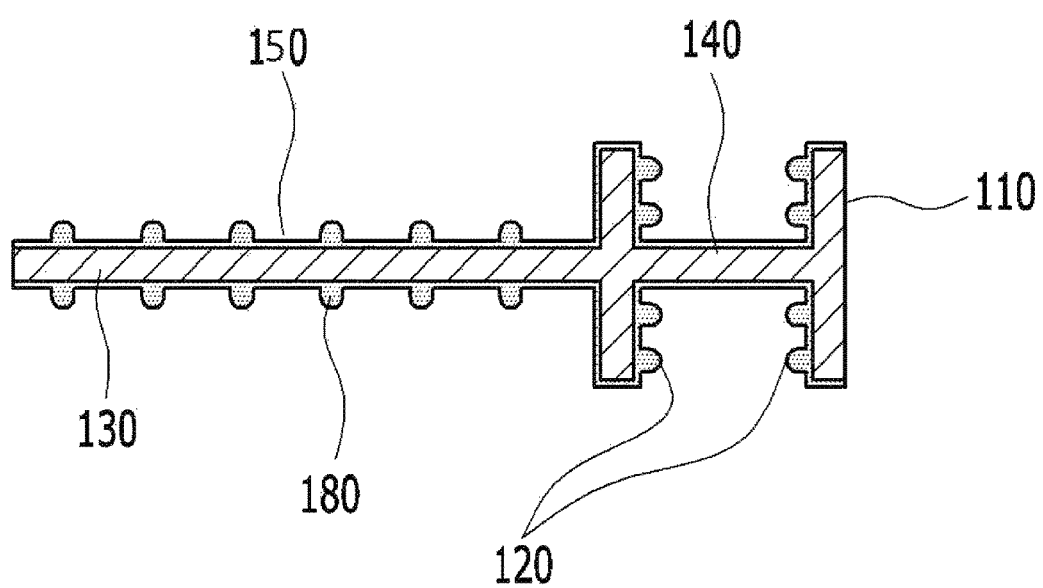
FIG. 3 illustrates a cross-sectional view taken along line A-A' of FIG. 2.
Figure 4:
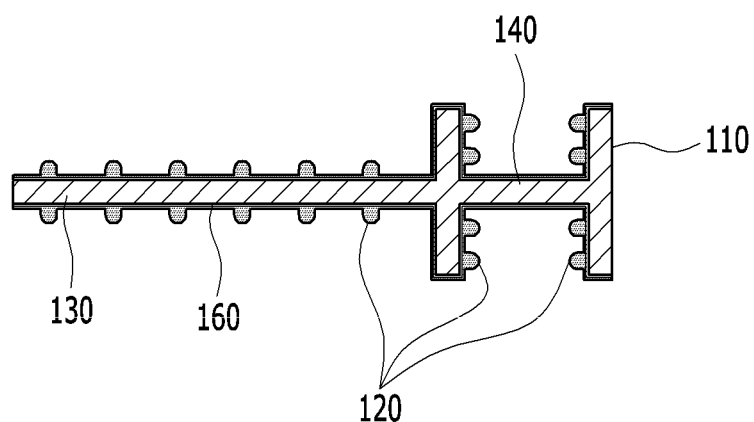
FIG. 4 illustrates a cross-sectional view taken along line A-A' of FIG. 2 in case of a mouthpiece type of electric toothbrush according to another exemplary embodiment of the present invention.
Figure 5:
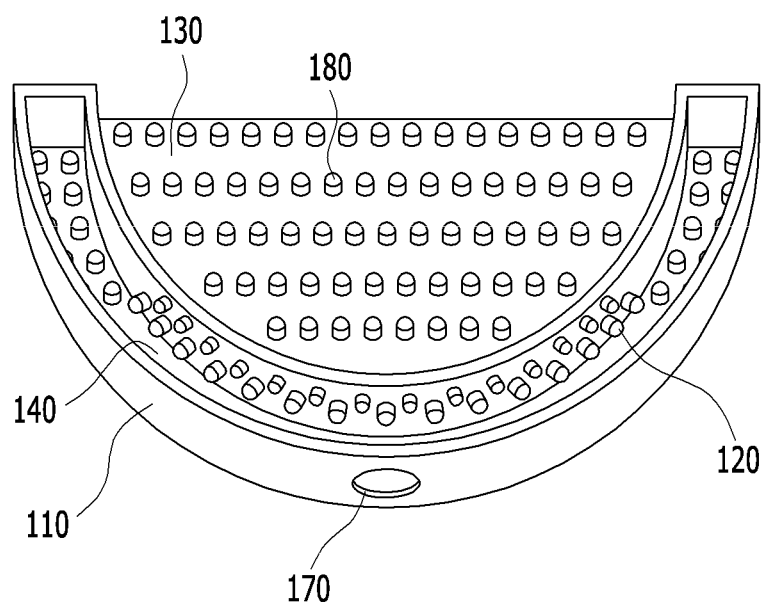
FIG. 5 illustrates a detailed schematic diagram of a housing of a mouthpiece type of electric toothbrush according to an exemplary embodiment of the present invention.
Figure 6:
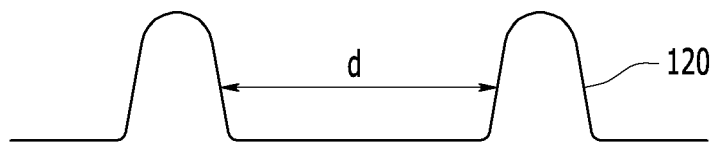
FIG. 6 illustrates protrusions of a mouthpiece type of electric toothbrush according to an exemplary embodiment of the present invention.
Figure 7:
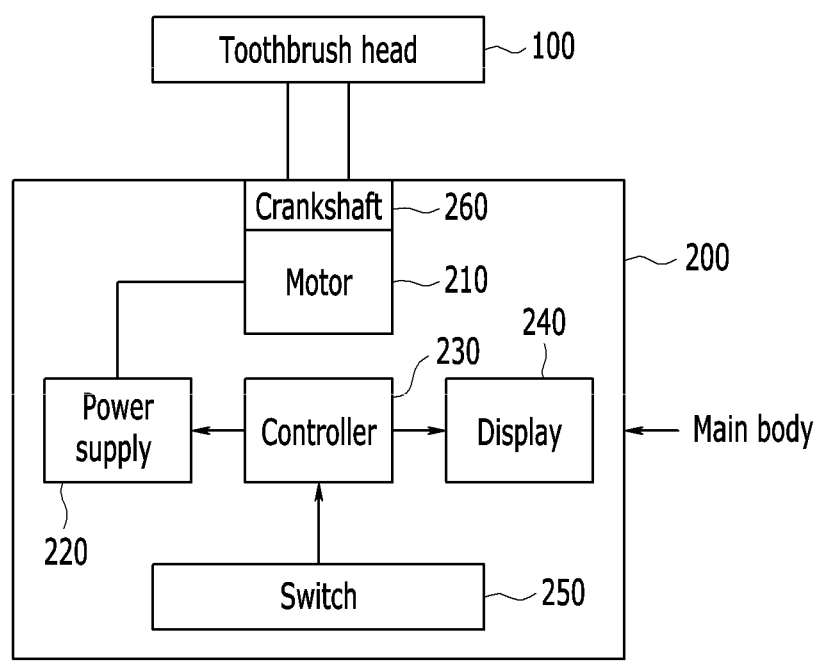
FIG. 7 illustrates an inner block diagram of a main body of a mouthpiece type of electric toothbrush according to an exemplary embodiment of the present invention.

FIG. 1 illustrates a schematic diagram of a mouthpiece type of electric toothbrush according to an exemplary embodiment of the present invention, FIG. 2 illustrates a schematic diagram of a toothbrush part of a mouthpiece type of electric toothbrush according to an exemplary embodiment of the present invention, FIG. 3 illustrates a cross-sectional view taken along line A-A' of FIG. 2, FIG. 4 illustrates a cross-sectional view taken along line A-A' of FIG. 2 in case of a mouthpiece type of electric toothbrush according to another exemplary embodiment of the present invention, FIG. 5 illustrates a detailed schematic diagram of a housing of a mouthpiece type of electric toothbrush according to an exemplary embodiment of the present invention, FIG. 6 illustrates protrusions of a mouthpiece type of electric toothbrush according to an exemplary embodiment of the present invention, and FIG. 7 illustrates an inner block diagram of a main body of a mouthpiece type of electric toothbrush according to an exemplary embodiment of the present invention.

Referring to FIG. 1 to FIG. 7, a mouthpiece type of electric toothbrush according to an exemplary embodiment of the present invention includes a toothbrush head 100 and a main body 200.

The toothbrush head 100 includes a mouthpiece-shaped housing 110 which is provided with upper and lower openings and a blocked intermediate portion 140, wherein a plurality of first silicone protrusions 120 are arranged to be spaced apart from each other by a predetermined interval along an inner wall surface of the housing in the upper and lower openings.

The toothbrush head 100 includes a plurality of water-containing pads 150 which are disposed between the first silicone protrusions 120 to absorb water. Accordingly, toothpaste may be easily spread, and after a hydrophilic material is coated on a silicone layer or a water-containing pad is attached thereto, when the toothbrush head is used after being soaked in an antiseptic solution, the oral cavity may be disinfected.

The toothbrush head 100 further includes a tongue-cleaning portion 130 for cleaning an upper surface of the tongue and the palate, and the tongue-cleaning portion 130 is provided in an inner concave portion of the housing 110.

A plurality of second silicone protrusions 180 are respectively formed on upper and lower portions of the tongue-cleaning portion 130 by a predetermined internal. A plurality of protrusions are formed on opposite surfaces of an inner intermediate wall of the housing 110 as portions of the housing 110 which molars contact, and a plurality of protrusions are formed on lateral surfaces of an inner wall of the housing 110 as portions of the housing 110 which incisors contact.

A framework of the housing 110 is formed of a plastic material, and an outer skin thereof is formed of a silicone material. Accordingly, the shape of the mouthpiece is easily maintained, and since a portion of the housing which the gum and the teeth contact is formed of the silicone material, the housing may softly contact.

The first and second silicone protrusions 120 and 180 are disposed to have a predetermined interval so that foreign matter may pass therethrough, and to have a bumpy surface so as to be easily cleaned, and they may be formed to have various shapes, if necessary.

A groove for a detachable coupling with the main body is formed in the housing 110.

Referring to FIG. 4, a toothbrush head 100 according to another exemplary embodiment of the present invention may include a silicone layer on which the first silicone protrusions are formed in the mouthpiece-shaped housing, and an air layer 160 into which air may be injected and which is disposed between the housing and the silicone layer.

As described above, the mouthpiece type of electric toothbrush is adjustable to correspond to a size of a user's mouth or oral cavity by adjusting an air amount of the air layer 160 provided at the lower portion of the silicone layer.

Both the water-containing pad 150 and the air layer 160 may be applied, as necessary.

The main body 200 has a detachable structure with respect to the toothbrush head 100, and transmits a vibration to the toothbrush head 100. Attachment and detachment of the main body 200 and the toothbrush head 100 are performed through a groove 170, and a structure for the attachment and the detachment may be variously modified.

The main body 200 includes a motor 210, a power supply 220, a controller 230, a display 240, a switch 250, and a crankshaft 260.

An operation such as power supply or vibration strength is selected by the switch 250. The controller 230 controls the power supply 220 and drives the motor 210 depending on the selection of the switch 250. The power supply 220 includes a battery, and supplies electric power depending on control of the controller 230. The motor 210 which is a vibration motor generates a vibration when electric power is supplied thereto.

The crankshaft 260 allows the vibration of the motor 210 to be moved up or down. As necessary, whether to operate the crankshaft 260 may be selected by the switch 250.

The display 240 may display an operating state, a vibration intensity, etc. The configuration of the main body 200 may be variously changed.

Hereinafter, operations of the mouthpiece type of electric toothbrush according to the exemplary embodiment of the present invention will be described.

When the toothbrush head 100 soaked in an antiseptic solution is used, it is combined with the main body 200.

In this case, since the water-containing pad 150 is a state that it has absorbed the antiseptic solution, the toothpaste is easily spread, and the antiseptic solution is spread inside the mouth, thereby disinfecting the oral cavity.

Children, the disabled, or other users who use the electric toothbrush apply electric power to the mouthpiece type of electric toothbrush by selection of the switch, and then they put the toothbrush head 100 in the oral cavity and shut their mouths.

Thus, the user's teeth including the user's upper and lower teeth are inserted in the openings of the upper and lower portions of the housing 110. That is, the molars are positioned at opposite sides of the housing 110, and the incisors are positioned at the intermediate portion of the housing. Then, the user's teeth, tongue, palate, and gums contact the first and second silicone protrusions 120 and 180.

In such a state, when an operation button of the switch 250 is pushed, the controller 230 controls the power supply 220 and drives the motor 210 according to the selection of the switch 250.

The motor 210 is the vibration motor, and when electric power is supplied thereto, it generates a vibration, and the generated vibration is transmitted to the toothbrush head 100 through the crankshaft 260. In this case, the crankshaft 260 may be selectively operated.

Thus, the housing 110 of the toothbrush head 100 is vibrated such that the first and second silicone protrusions 120 and 180 are vibrated.

When the first and second silicone protrusions 120 and 180 are vibrated, the user's teeth, tongue, palate, and gums are cleaned.

In this case, the foreign matter is discharged through spaces between the first and second silicone protrusions 120 and 180.

Through the processes described above, the user's teeth, tongue, palate, and gums are cleaned.

Accordingly, while the user is merely holding the main body 200, the user's teeth, tongue, palate, and gums may be easily cleaned.

In this case, since the vibration thereof may increase by the crankshaft 260, even if the toothbrush head 100 is lightened, an excellent cleaning effect may be provided.

Further, it is possible to provide the mouthpiece type of electric toothbrush that may easily spread toothpaste through a water-containing pad and that is adjustable to correspond to a size of a user's mouth or oral cavity by adjusting an air amount of an air layer provided at a lower portion of a silicone layer thereof.

In addition, it is possible to prevent growth of bacteria and to easily perform sterilization and disinfection by forming the toothbrush head with the silicone material.

It is also possible to make the gums healthy by massaging the gums while brushing the teeth.

While this invention has been described in connection with what is presently considered to be practical exemplary embodiments, it is to be understood that the invention is not limited to the disclosed embodiments. On the contrary, it is intended to cover various modifications and equivalent arrangements included within the spirit and scope of the appended claims.

The invention claimed is:

1. A mouthpiece type of electric toothbrush, comprising:
a toothbrush head that includes a mouthpiece-shaped housing which is provided with upper and lower openings and a blocked intermediate portion, wherein a plurality of first silicone protrusions are arranged to be spaced apart from each other by a predetermined interval along an inner wall surface of the housing in the upper and lower openings, and a plurality of water-containing pads for absorbing water are provided between the plurality of first silicone protrusions; and
a main body that is detachable from the toothbrush head and that is configured to transmit a vibration to the toothbrush head,
wherein the toothbrush head includes a silicone layer on which the first silicone protrusions are formed in the mouthpiece-shaped housing, and an air layer into which air is injected and which is disposed between the housing and the silicone layer.

2. The mouthpiece type of electric toothbrush of claim 1, wherein
the main body includes:
a motor that vibrates when electric power is applied thereto; and
a crankshaft that allows vibration of the motor to be moved up or down.

3. The mouthpiece type of electric toothbrush of claim 2, wherein
the toothbrush head includes a tongue-cleaning portion that is configured to clean an upper surface of a tongue and a palate and that is provided in an inner concave portion of the housing.

4. The mouthpiece type of electric toothbrush of claim 3, wherein
a plurality of second silicone protrusions are respectively formed on upper and lower portions of the tongue-cleaning portion by a predetermined internal.

5. The mouthpiece type of electric toothbrush of claim 4, wherein
a plurality of protrusions are formed on opposite surfaces of an inner intermediate wall of the housing as portions of the housing which molars contact, and a plurality of protrusions are formed on lateral surfaces of an inner wall of the housing as portions of the housing which incisors contact.

6. The mouthpiece type of electric toothbrush of claim 2, wherein the first silicone protrusions are disposed to have
a predetermined interval for foreign matter to pass therethrough, and to have a bumpy surface so as to be easily cleaned.

7. The mouthpiece type of electric toothbrush of claim 1, wherein the first silicone protrusions are disposed to have
a predetermined interval for foreign matter to pass therethrough, and to have a bumpy surface so as to be easily cleaned.

* * * * *